United States Patent [19]

Nakatani

[11] Patent Number: 5,370,953

[45] Date of Patent: Dec. 6, 1994

[54] ELECTROPHOTOSENSITIVE MATERIAL

[75] Inventor: Kaname Nakatani, Osaka, Japan

[73] Assignee: Mita Industrial Co., Ltd., Osaka, Japan

[21] Appl. No.: 979,643

[22] Filed: Nov. 20, 1992

[30] Foreign Application Priority Data

Nov. 28, 1991 [JP] Japan .................. 3-314629

[51] Int. Cl.$^5$ .................. J03H 5/09; J03H 5/147
[52] U.S. Cl. .................. 430/58; 430/66; 430/77; 430/83
[58] Field of Search .................. 430/58, 77, 66, 83; 548/145

[56] References Cited

U.S. PATENT DOCUMENTS

| | | | |
|---|---|---|---|
| 3,189,447 | 6/1965 | Neugebauer et al. | 430/77 |
| 3,666,683 | 5/1972 | Maeder et al. | 548/145 |
| 4,758,488 | 7/1988 | Johnson et al. | |
| 5,294,510 | 3/1994 | Ueda et al. | 430/59 |

FOREIGN PATENT DOCUMENTS

| | | | |
|---|---|---|---|
| 0426445 | 5/1991 | European Pat. Off. | |
| 4-46350 | 2/1992 | Japan | 430/83 |

OTHER PUBLICATIONS

Patent Abstracts of Japan, vol. 12, No. 427 (P-784)(3274), Nov. 11, 1988, to Tamaki.
Database WPIL Derwent, AN 83-60461K, relating to Japanese Patent Publication No. 58-082252, May 17, 1983.
Database WPIL Derwent, AN 85-180853, relating to Japanese Patent Publication No. 60108860, Jun. 14, 1985.

Primary Examiner—Christopher D. Rodee
Attorney, Agent, or Firm—Beveridge, DeGrandi, Weilacher & Young

[57] ABSTRACT

The invention presents an electrophotosensitive material comprising a conductive substrate, a photosensitive layer formed on the conductive substrate, and, if necessary, a surface protective layer formed on the photosensitive layer, wherein an oxadiazole derivative expressed in a general formula (I):

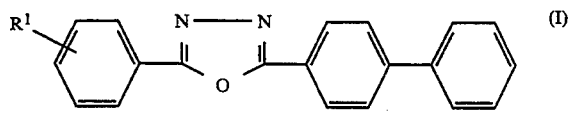

where $R^1$ denotes an alkyl group, is contained as an electron transfer substance on the photosensitive layer and/or surface protective layer. This photosensitive material enhances the electron transfer capability, and hence the sensitivity is improved. At the same time, the residual potential of the photosensitive material is lowered, and the stability and durability against repeated exposures are enhanced.

12 Claims, No Drawings

ELECTROPHOTOSENSITIVE MATERIAL

BACKGROUND OF THE INVENTION

The present invention relates to an electrophotosensitive material for use in electrostatic process copying machine, laser beam printer or the like.

In an image forming apparatus making use of electrophotographic technology such as electrostatic process copying machine, an electrophotosensitive material forming a photosensitive layer on a substrate having a conductive property is employed.

When the electrophotosensitive material is exposed to light with the surface being charged positively or negatively, the illuminated portion is electrically charged, that is, a hole and an electron are formed, one of them is transferred up to the surface of the photosensitive layer to neutralize the electric charge of the surface, while the other is transferred up to the conductive substrate to be biased. On the other hand, in the unilluminated portion, the electric charge is left over, and a pattern of the charge corresponding to the exposure image is formed on the surface of the photosensitive material, that is, an electrostatic latent image is formed.

As the electrophotosensitive material, the so-called function separate type separating the charge generating function and the charge transfer function by combining a charge generating substance for generating an electric charge by irradiation with light and a charge transfer substance for transferring the generated charge is widely employed because the sensitivity may be enhanced easily. The electrophotosensitive material of function separate type is available in the laminate type having a laminate photosensitive layer comprising a charge generating layer containing the charge generating substance and a charge transfer layer containing the charge transfer substance, which is formed on the surface of a conductive substrate, and in the single layer type having a single layer type photosensitive layer containing the charge generating substance and charge transfer substance, which is formed on the surface of a conductive substrate.

Besides, in the electrophotosensitive material of function separate type, the organic photosensitive material, of which the entire photosensitive layer of the single layer type or laminate type, is formed on the surface of the conductive substance. The photosensitive material is composed of an organic layer wherein the functional components of charge generating substance, charge transfer substance and others are contained in the binding resin alternatively the complex photosensitive material with a part of the photosensitive layer of the laminate type as an organic layer is preferably used because the margin of selection of substance is wide, productivity is excellent, and the degree of freedom of functional design is high.

On the surface of the electrophotosensitive material, moreover, a surface protective layer may be laminated in order to prevent its mechanical wear or optical deterioration.

In the conventional electrophotosensitive material, however, the apparent charge generating efficiency was low, and therefore the sensitivity was not achieved as designed. Yet, if provided with a surface protective layer, the residual potential was high, and the stability and durability were lowered when exposed repeatedly.

These problems are attributable to the fact that the charge transfer substance hitherto employed is mostly the electron donor substance (hole transfer substance) which is excellent in the hole transfer capacity but is inferior in the capacity for transferring electrons.

That is, in the state where the electrons charged by exposure are left over in the photosensitive layer without being transferred, motion of the holes is also impeded by the coulombic force of the electrons, and the rate of rebonding of electrons and holes increased, which results in lowering of the quantity of holes or electrons contributing to formation of the electrostatic latent image, that is to say, the apparent charge generating efficiency is lowered and the sensitivity of the photosensitive material drops. Moreover, when a large quantity of electrons is left over, the residual potential of the photosensitive material is heightened by their accumulation.

It has been recently studied, accordingly, to contain an electron receptor substance (electron transfer substance) such as diphenoquinone derivative expressed in formula (II) in the photosensitive layer or surface protective layer:

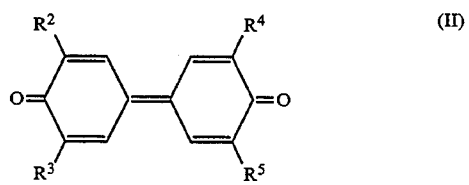

where $R^2$, $R^3$, $R^4$, $R^5$ are the same or different alkyl groups.

However, hitherto used electron transfer substances such as diphenoquinone derivatives above are (1) inferior in compatibility with binding resin and others, and (2) characterized by such a color as to impede transmission of light, and hence a large portion could not be added to the photosensitive layer or surface protective layer. The conventional photosensitive material, therefore, could not sufficiently exhibit the electron transfer capability, and the foregoing problems have not been completely solved.

SUMMARY OF THE INVENTION

It is hence a primary object of the invention to present an electrophotosensitive material having a higher sensitivity than in the conventional materials.

It is another object of the invention to present an electrophotosensitive material lowered in the residual potential, and enhanced in stability and durability if exposed to light repeatedly.

To achieve the above objects, the invention presents an electrophotosensitive material wherein the photosensitive layer formed on a conductive substrate contains an oxadiazole derivative expressed in a formula (I):

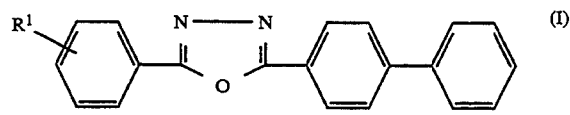

where $R^1$ denotes an alkyl group.

The invention also presents an electrophotosensitive material further comprising a surface protective layer on the photosensitive layer, wherein the photosensitive layer and/or surface protective layer contains an oxadiazole derivative expressed in formula (I).

The oxadiazole derivative expressed in formula (I) is, as clear from this formula, an electron receptor possessing a broader pi-electron conjugate system as compared with various known electron receptor substances, such as the diphenoquinone derivative expressed in formula (II), and is hence particularly excellent in the electron transfer capability.

Moreover, the oxadiazole derivative in formula (I) is, as clear from this formula, large in asymmetricity of molecules and is hence excellent in compatibility with the binding resin for composing the photosensitive layer or surface protective layer, so that much may be contained in these layers.

Still more, since the oxadiazole derivative is colorless and transparent or pale yellow, and does not impede light transmission, and therefore when contained at a high concentration in the photosensitive layer or surface protective layer, adverse effects are not caused on the sensitivity characteristic of the electrophotosensitive material.

Therefore, in the electrophotosensitive material of the invention containing the oxadiazole derivative expressed in formula (I), the electron transfer capability may be extremely improved, and the rate of rebonding of electrons and holes is accordingly decreased, and the apparent charge generating efficiency is closer to the actual value, and the sensitivity of the photosensitive material is enhanced. Besides, the residual potential of the photosensitive material is lower (that is, the quantity of electrons left over in the layer is decreased), and stability and durability by repeated exposures are improved.

DETAILED DESCRIPTION OF THE INVENTION

In the formula (I), $R^1$ denotes an alkyl group, and in particular a lower alkyl group with two or more carbon atoms, preferably two to six carbon atoms are favorably used, such as ethyl group, propyl group, isopropyl group, butyl group, isobutyl group, t-butyl group, pentyl group and hexyl group.

A preferred example of the oxadiazole derivative includes a compound expressed in a formula (Ia).

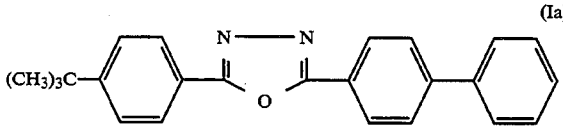

(Ia)

The constitution of the invention may be applied to various types of electrophotosensitive material possessing an organic layer capable of containing the above oxadiazole derivative (hereinafter called the "specific layer"), and examples of the specific layer include, among others, the following:

(1) A single layer type photosensitive layer possessing a charge generating substance and a hole transfer substance in the binding resin.

(2) A charge generating layer in a laminate negatively charged organic photosensitive layer laminating a charge generating layer containing a charge generating substance in the binding resin, and a hole transfer layer containing a hole transfer substance in the binding resin, on a conductive substrate in this sequence.

(3) A charge generating layer in a laminate positively charged organic photosensitive layer laminating a hole transfer layer containing a hole transfer substance in the binding resin, and a charge generating layer containing a charge generating substance in the binding resin, on a conductive substrate in this sequence.

(4) A surface protective layer formed on a photosensitive layer of laminate type or single layer type.

The content ratio of the oxadiazole derivative in the specific layer is not particularly limited in the invention, but it is desired to be in the following range for 100 parts by weight of the binding resin:

10 to 150 parts by weight in the organic photosensitive layer of single layer type of (1);

10 to 100 parts by weight in the charge generating layer in the laminate negatively charged organic photosensitive layer of (2);

10 to 100 parts by weight in the charge generating layer in the laminate positively charged organic photosensitive layer of (3); and 10 to 100 parts by weight in the surface protective layer of (4).

If the content of the oxadiazole derivative in each specific layer is lower than the specified range, the additive effect of the oxadiazole derivative is insufficient, and the sensitivity of the photosensitive material, and stability and durability may not be sufficiently improved. If the content of the oxadiazole derivative in each specific layer exceeds the specified range, the amount of the binding resin becomes relatively small, and the film forming performance is lowered, and the specific layer becomes fragile, and the durability of the photosensitive material may be impaired. Moreover, when the content of the oxadiazole derivative exceeds the specified range, the light transmissivity of the specific layer is lowered, and the sensitive characteristic of the photosensitive layer may be affected.

In the electrophotosensitive material of the invention, other known electron transfer substances may be combined so far as not to impede the additive effect of the oxadiazole derivative. Examples of other electron transfer substance, aside from the diphequinone derivative expressed in formula (II), may include malononitrile, thiopyran compound, tetracyanoethylene, 2,4,8-trinitrothioxanthone, 3,4,5,7-tetranitro-9-fluorenone, dinitrobenzene, dinitroanthracene, dinitroacridine, nitroanthraquinone, dinitroanthraquinone, succinic anhydride, maleic anhydride, dibromomaleic anhydride, etc.

The electrophotosensitive material of the invention is similar to the prior art except for the above constitution. That is, as the conductive substrate, various materials possessing electric conductivity may be used, for example, aluminum, copper, tin, platinum, silver, vanadium, molybdenum, chromium, cadmium, titanium, nickel, palladium, indium, stainless steel, brass, other metals, plastics evaporated or laminated with such metals, and glass coated with aluminum iodide, tin oxide, indium oxide or the like.

The conductive substrate may be in a form of a sheet, drum or others, and either the substrate itself may be conductive or the surface of the substrate may be conductive. Besides, it is desired to use the conductive substrate having a sufficient mechanical strength in actual use.

As stated above, in the single layer type photosensitive layer composed by containing charge generating substance and hole transfer substance in the binding resin, the content ratio of the charge generating substance to 100 parts by weight of the binding resin is desired to be in a range of 2 to 20 parts by weight, more preferably in a range of 3 to 15 parts by weight. On the other hand, the content ratio of the charge transfer substance to 100 parts by weight of the binding resin is desired to be in a range of 40 to 200 parts by weight, more preferably in a range of 50 to 100 parts by weight.

If the charge generating substance is less than 2 parts by weight or the charge transfer substance is less than 40 parts by weight, the sensitivity of the photosensitive material may be insufficient, or the residual potential becomes large. If the charge generating substance exceeds 20 parts by weight or the charge transfer substance exceeds 200 parts by weight, the wear resistance of the photosensitive material may not be sufficient.

The single layer type photosensitive layer may be formed in a proper thickness, and is usually formed in a range of 10 to 50 $\mu$m, in particular 15 to 25 $\mu$m.

The charge generating layer provided in the laminate negatively charged photosensitive material or laminate positively charged photosensitive material is composed by including a charge generating substance in the binding resin as mentioned above, wherein the charge generating layer is a specific layer containing an oxadiazole derivative.

The content ratio of the charge generating substance to 100 parts by weight of the binding resin in the charge generating layer is desired to be 5 to 500 parts by weight, preferably in a range of 10 to 300 parts by weight. If the charge generating substance is less than 5 parts by weight, the charge generating capacity is too small, or if exceeding 500 parts by weight, the adhesion with the other adjacent layer or the substrate is lowered.

The charge generating layer is desired to be formed in a thickness of 0.01 to 5 $\mu$m, more preferably in a range of 0.1 to 3 $\mu$m.

If, incidentally, the charge generating layer is not a specific layer containing oxadiazole derivative, this charge generating layer may be formed by, for example, forming a thin film of charge generating substance by a vapor phase growth method such as a vacuum deposition process.

The hole transfer layer for composing the laminate negatively charged photosensitive material or laminate positively charged photosensitive material together with the charge generating layer may be added at various rates to the binding resin so far as not to impede the transfer of poles and not to crystallize them, but it is desired to contain the hole transfer substance at a rate of 10 to 500 parts by weight to 100 parts by weight of the binding resin, or preferably in a range of 25 to 200 parts by weight, so that the holes generated in the charge generating layer by irradiation with light may be transferred easily.

The thickness of the hole transfer layer is desired to be 2 to 100 $\mu$m, in particular 5 to 50 $\mu$m.

As the binding resin for composing the layers, various binding resins hitherto used in charge generating layers in organic electrophotosensitive material may be employed, and in particular the binding resins excellent in compatibility with oxadiazole derivative are preferred.

Preferred examples of the binding resin include styrene copolymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, vinyl chloride-vinyl acetate copolymer, polyester, alkyd resin, polyamide, polyurethane, polycarbonate, polyallylate, polysulfone, diallylphthalate resin, ketone resin, polyvinyl butyral resin, polyether resin, other thermoplastic resins; silicone resin, epoxy resin, phenol resin, urea resin, melamine resin, other crosslinking thermosetting resins; and epoxyacrylate, urethaneacrylate and other photosetting resins. These binding resins may be used either alone or in mixture of two or more kinds.

As the charge generating substance contained in the charge generating layer in the single layer type photosensitive layer or laminate type photosensitive layer, conventional materials may be used, including selenium, selenium-tellurium, selenium-arsenic, armophous silicon, pyrylium salt, azo compound, disazo compound, phthalocyanine compound, anthanthrone compound, perylene compound, indigo compound, triphenyl methane compound, threne compound, toluidine compound, pyrazoline compound, perylene compound, quinacridone compound, pyrolopyrol compound, etc. These charge generating substances may be used either alone or in combination of two or more kinds so as to possess an absorption wavelength region in a desired region.

The hole transfer substance contained the single layer type sensitive layer or the hole transfer layer of laminate type sensitive layer may be, for example, oxadiazole compound such as 2,5-di(4-methylaminophenyl) and 1,3,4-oxadiazole, styryl compound such as 9-(4-diethylaminostyryl)anthracene, carbazole compound such as polyvinyl carbazole, pyrazoline compound such as 1-phenyl-3-(p-dimethylaminophenyl)pyrazoline, hydrazone compound, triphenylamine compound, indole compound, oxazole compound, isooxazole compound, thiazole compound, thiadiazole compound, imidazole compound, pyrazole compound, triazole compound, and other cyclic compounds containing nitrogen, and condensation polycyclic compounds.

These hole transfer substances may be used either alone or in mixture of two or more kinds. Meanwhile, when using a hole transfer substance possessing a film forming property such as polyvinyl carbazole, the binding resin is not always necessary.

Each layer may contain additives such as fluorene compound, anti-oxidant, ultraviolet absorber, other deterioration preventives, and plasticizers. To enhance the sensitivity of the photosensitive material, moreover, for example, a known sensitizer such as terphenyl, halonaphthoquinone and acenaphthylene may be combined with the charge generating substance.

The surface protective layer is composed of urethane resin or epoxy resin relatively high in hardness and superior in transparency, or silicone resin or similar resin excellent in mechanical strength, stable chemically, and excellent in transparency, in order to maintain the wear resistance or durability of the photosensitive material. Besides, other resins may be also combined so far as not to impair the membrane characteristics.

Examples of other resins include curing-type acrylic resin; alkyd resin; unsaturated polyester resin; diallylphthalate resin; phenol resin; urea resin; benzoguanamine resin; melamine resin; styrene polymer; acrylic polymer; styrene-acrylic copolymer; polyethylene, ethylene-vinyl acetate copolymer, chlorinated polyethylene, polypropylene, ionomer, and other olefin polymers; polyvinyl chloride; vinyl chloride-vinyl acetate copolymer; polyvinyl acetate; saturated polyester; polyamide; thermoplastic polyurethane resin; polycarbonate; polyallylate; polysulfone; ketone resin; polyvinyl butyral resin; and polyether resin.

In the surface protective layer, a transparent conductive substance such as $Sb/SnO_2$ may be dispersed. The transparent conductive substance is desired to be used at a range of 10 to 40 parts by weight to 100 parts by weight of the resin. The surface protective layer may also contain additives such as anti-oxidant, ultraviolet absorber, other deterioration preventives and plasticizers.

The thickness of the surface protective layer is desired to be formed in a range of 0.1 to 10 μm, preferably 0.5 to 10 μm.

Of these layers, a barrier layer may be formed between adjacent layers so far as not to impede the characteristics of the photosensitive material.

To form these layers by a coating method, the specified substances and binding resins are, together with proper solvents, dispersed and mixed in the known methods by using, for example, roll mill, ball mill, attriter, paint shaker or ultrasonic disperser to prepare a coating solution, which is applied and dried by a bar coating method, spin coating method, dip coating method, or other known method mentioned above.

As the solvents for preparing the coating solution, various organic solvents may be used, for example, alcohols such as methanol, ethanol, isopropanol and butanol, aliphatic hydrocarbons such as n-hexane, octane and cyclohexane, aromatic hydrocarbons such as benzene, toluene and xylene, halogenated hydrocarbons such as dichloromethane, dichloroethane, carbon tetrachloride and chlorobenzene, ethers such as dimethyl ether, diethyl ether, tetrahydrofurane, ethylene glycol dimethyl ether and diethylene glycol dimethyl ether, ketones such as acetone, methylethylketone and cyclohexanone, esters such as ethyl acetate and methyl acetate, dimethyl formaldehyde, dimethyl formamide, and dimethyl sulfoxide. These solvents may be used either alone or in mixture of two or more kinds.

Furthermore, to improve the dispersing property or coating performance of the hole transfer substance or charge generating substance, surface active agent, leveling agent and others may be used.

As mentioned above, the charge generating layer of the laminate type photosensitive layer may be formed by vacuum evaporation of the charge generating substance.

EXAMPLES

The invention is described in detail below by referring to Examples and Comparative Examples, but is not limited to only the Examples.

EXAMPLE 1

5 parts by weight of metal-free phthalocyanin (charge generating substance), 75 parts by weight of p-diethylaminobenzaldehyde diphenylhydrazone (hole transfer substance), 50 parts by weight of oxadiazole derivative (charge transfer substance) expressed in formula (Ia), and 100 parts by weight of polyester resin (Vylon 200, tradename of Toyobo Co.) (binding resin) were dissolved in 900 parts by weight of cyclohexane. The obtained solution was applied on the surface of an aluminum cylinder pipe of 78 mm in outside diameter and 75 mm in inside diameter, dried at 110° C., whereby a photosensitive material layer of about 20 μm in thickness was formed, and a positively charged electrophotosensitive material which is single layer type was obtained.

COMPARATIVE EXAMPLE 1

A single-layer type positively charged electrophotosensitive material was obtained in the same procedure as in Example 1, except that oxadiazole derivative was not added to the solution for a single-layer photosensitive layer.

EXAMPLE 2

100 parts by weight of metal-free phthalocyanin (charge generating substance), 30 parts by weight of oxadiazole derivative expressed in formula (Ia), and 50 parts by weight of polyvinyl butyral (model BH-3 of Sekisui Chemical Co., binding resin) were dispersed in 3500 parts by weight of n-butyl alcohol. The obtained dispersion liquid was applied on the surface of aluminum cylinder pipe same as in Example 1, dried at 110° C., whereby a charge generating layer of about 0.4 μm in thickness was formed.

Consequently, 100 parts by weight of p-diethylaminobenzaldehyde diphenylhydrazone (hole transfer substance), and 100 parts by weight of polyester resin (Vylon 200, tradename of Toyobo Co.) (binding resin) were dissolved in 900 parts by weight of toluene, and the obtained solution was applied on the surface of the charge generating layer, dried at 110° C., and a hole transfer layer of about 20 μm in thickness was formed, and a laminate type negatively charged photosensitive material was obtained.

COMPARATIVE EXAMPLE 2

A laminate type negatively charged electrophotosensitive material was obtained in the same manner as in Example 2, except that oxadiazole derivative was not added to the solution for charge generating layer.

EXAMPLE 3

100 parts by weight of p-diethylaminobenzaldehyde diphenylhydrazone (hole transfer substance) and 100 parts by weight of polyallylate resin (model U-100 of Unitika Co.) (binding resin) were dissolved in 900 parts by weight of dichloromethane. The obtained solution was applied on the surface of aluminum cylinder pipe same as in Example 1, dried at 100° C., whereby a hole transfer layer of about 22 μm in thickness was formed.

Consequently, 100 parts by weight of dibromo anthanthrone (charge generating substance), 50 parts by weight of oxadiazole derivative expressed in formula (Ia), and 50 parts by weight of polyvinylbutyral (model 300K of Denki Kagaku Kogyo Co.) (binding resin) were dispersed in 3500 parts by weight of n-butyl alcohol. The obtained dispersion liquid was applied on the surface of the hole transfer layer, dried at 110° C., whereby a charge generating layer of about 0.3 μm in thickness was formed.

Successively, a commercially available silicone resin type hard coat agent (model NSC-1272 of Nippon Seika Co.) was applied on the surface of the charge generating layer, heated at 120° C., whereby a surface protective layer of about 2.5 μm in thickness was formed, and a laminate type positively charged electrophotosensitive material was obtained.

EXAMPLE 4

A laminate type positively charged electrophotosensitive material was obtained in the same procedure as in Example 3, except that oxadiazole derivative expressed in formula (Ia) was added to the silicone resin type hard coat agent. The content of oxadiazole derivative was 40 parts by weight to 100 parts by weight of the hard coat agent.

EXAMPLE 5

A laminate type positively charged electrophotosensitive material was obtained in the same procedure as in Example 3, except that oxadiazole derivative was not added to the solution for charge generating layer, and that oxadiazole derivative expressed in formula (Ia) was added to the silicone resin type hard coat agent.

COMPARATIVE EXAMPLE 3

A laminate type positively charged electrophotosensitive material was obtained in the same procedure as in Example 3, except that oxadiazole derivative was not added to either solution for the charge generating layer or silicone resin type hard coat agent.

EVALUATION TEST

Electrophotosensitive materials obtained in the Examples and Comparative Examples were mounted on the electrostatic copying testing apparatus (Cincia 30M, tradename of Gentek Co.), and the surface potential Vls.p. (V) was measured by charging the surface positively or negatively. In addition, using the halogen lamp, which is an exposure light source of this apparatus, the surface of the electrophotographic sensitive materials was exposed in the conditions of the exposure intensity of 100 lux and exposure time of 40 ms, and the time until the surface potential Vls.p. became ½ was determined, and the sensitivity S1 (1/lux-sec) of the sensitive materials was determined from the result.

Moreover, the electrophotosensitive materials were mounted on an electrostatic process copying machine (model DC-3285 of Mira Industrial Co., Ltd.), and images were formed continuously on 1000 sheets. The electrophosensitive materials were mounted again on the electrostatic process copying testing apparatus mentioned above, and the surface potential Vls.p. (V) and sensitivity S2 (1/lux-sec) were determined, and the rate of change (%) from the initial value was calculated in the following formulae:

$$\text{Surface potential change rate } \delta V_{s.p.} (\%) = \frac{V2_{s.p.} - V1_{s.p.}}{V1_{s.p.}} \times 100$$

$$\text{Sensitivity change rate } \delta S (\%) = \frac{S2 - S1}{S1} \times 100$$

The results are shown in Table 1.

TABLE 1

| | Surface potential $V1_{s.p.}$ | Change rate $\delta V_{s.p.}$ | Sensitivity S1 | Change rate $\delta S$ |
|---|---|---|---|---|
| Example 1 | +855 | −4.0 | 0.12 | −2.2 |
| Comparative Example 1 | +847 | −15.8 | 0.07 | −7.9 |
| Example 2 | −866 | −3.6 | 0.37 | −1.8 |
| Comparative Example 2 | −843 | −10.2 | 0.25 | −5.6 |
| Example 3 | +837 | −2.3 | 0.19 | −2.0 |
| Example 4 | +854 | −0.9 | 0.32 | −1.2 |
| Example 5 | +861 | −1.8 | 0.28 | −1.5 |
| Comparative Example 3 | +862 | −15.6 | 0.13 | −7.3 |

As known from the results in Table 1, the sensitive materials of Examples 1 to 5 were, as compared with the Comparative Examples having the same layer without containing oxadiazole derivative, similar in the initial surface potential Vls.p., but were higher in the sensitivity S1, and are hence known to have a higher sensitivity. Besides, from the results of change rate after repeated exposures, the photosensitive materials of Examples 1 to 5 are found to be excellent in both stability and durability as compared with the corresponding Comparative Examples.

What is claimed is:

1. An electrophotosensitive material, comprising: a conductive substrate; a single layer photosensitive layer formed on the conductive substrate, wherein the single layer photosensitive layer includes a charge generating substance and a hole transfer substance; and a surface protective layer formed on said single layer photosensitive layer, wherein said surface protective layer includes an oxadiazole derivative according to formula (1):

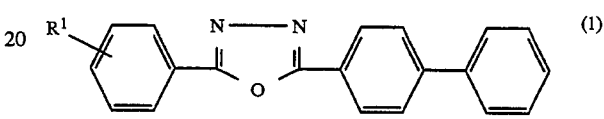

wherein $R^1$ denotes an alkyl group.

2. An electrophotosensitive material according to claim 1, wherein said single layer photosensitive layer includes an oxadiazole derivative according to formula (1).

3. The electrophotosensitive material according to claim 1, wherein the alkyl group is a member selected from the group consisting of: an ethyl group, a propyl group, an isopropyl group, a butyl group, an isobutyl group, a t-butyl group, a pentyl group, and a hexyl group.

4. The electrophotosensitive material according to claim 1, wherein the oxadiazole derivative is a compound represented by the following formula:

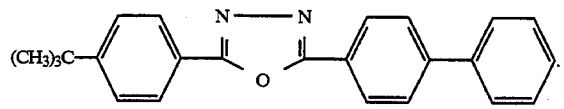

5. The electrophotosensitive material according to claim 1, wherein the surface protective layer has a thickness in the range of 0.1 to 10μm.

6. The electrophotosensitive material according to claim 1, wherein the surface protective layer has a thickness in the range of 0.5 to 10μm.

7. An electrophotosensitive material, comprising: a conductive substrate; a hole transfer layer on the conductive substrate; a charge generating layer formed on the hole transfer layer; and a surface protective layer formed on the charge generating layer, said surface protective layer including an oxadiazole derivative according to formula (1):

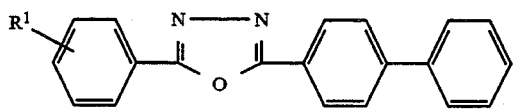

wherein R¹ denotes an alkyl group.

8. An electrophotosensitive material according to claim 7, wherein said charge generating layer includes a charge generating substance and an oxadiazole derivative according to formula (1 ).

9. The electrophotosensitive material according to claim 7, wherein the alkyl group is a member selected from the group consisting of: an ethyl group, a propyl group, an isopropyl group, a butyl group, an isobutyl group, a t-butyl group, a pentyl group, and a hexyl group.

10. The electrophotosensitive material according to claim 7, wherein the oxadiazole derivative is a compound represented by the following formula:

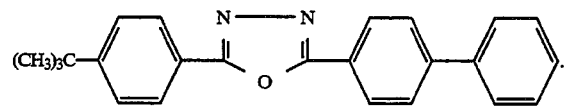

11. The electrophotosensitive material according to claim 7, wherein the surface protective layer has a thickness the range of 0.1 to 10μm.

12. The electrophotosensitive material according to claim 7, wherein the surface protective layer has a thickness in the range of 0.5 to 10 μm.

* * * * *